(12) United States Patent
Wu et al.

(10) Patent No.: US 9,945,776 B2
(45) Date of Patent: Apr. 17, 2018

(54) MAIL DETECTION DEVICE AND METHOD

(71) Applicants: CHINA COMMUNICATION TECHNOLOGY CO.,LTD., Shenzhen (CN); SHENZHEN VICTOOTH TERAHERTZ TECHNOLOGY CO.,LTD., Shenzhen (CN)

(72) Inventors: Guangsheng Wu, Shenzhen (CN); Yandong Zhang, Shenzhen (CN); Qing Ding, Shenzhen (CN)

(73) Assignees: China Communication Technology Co., Ltd., Shenzhen (CN); Shenzhen Victooth Terahertz Technology Co., Ltd., Shenzhen (CN)

( * ) Notice: Subject to any disclaimer, the term of this patent is extended or adjusted under 35 U.S.C. 154(b) by 14 days.

(21) Appl. No.: 15/315,604

(22) PCT Filed: Sep. 14, 2015

(86) PCT No.: PCT/CN2015/089536
§ 371 (c)(1),
(2) Date: Dec. 1, 2016

(87) PCT Pub. No.: WO2017/020402
PCT Pub. Date: Feb. 9, 2017

(65) Prior Publication Data
US 2017/0184495 A1 Jun. 29, 2017

(30) Foreign Application Priority Data
Aug. 4, 2015 (CN) .......................... 2015 1 0470876

(51) Int. Cl.
G01N 21/3581 (2014.01)
B07C 1/00 (2006.01)

(52) U.S. Cl.
CPC ........... *G01N 21/3581* (2013.01); *B07C 1/00* (2013.01); *B07C 2201/006* (2013.01);
(Continued)

(58) Field of Classification Search
CPC .............................. G01N 21/3581; B07C 1/00
See application file for complete search history.

(56) References Cited

U.S. PATENT DOCUMENTS

| 2012/0008148 A1* | 1/2012 | Pryce | ................... G01B 11/245 356/601 |
| 2013/0334421 A1* | 12/2013 | Itsuji | ..................... G01J 5/0205 250/341.8 |
| 2014/0252231 A1* | 9/2014 | Tomioka | ............ G01N 21/3581 250/338.1 |

\* cited by examiner

*Primary Examiner* — David Porta
*Assistant Examiner* — Mindy Vu
(74) *Attorney, Agent, or Firm* — Calfee, Halter & Griswold LLP

(57) ABSTRACT

The present invention discloses a mail detection device and method. The device comprises a broad-band terahertz generator, a collimator, a beam splitter, a fixed reflector, a movable reflector, a wave buncher, a matrix detector, an acquisition card and an information processing module; wherein the information processing module is used for generating a terahertz image of a mail to be detected according to the electric signals sent by the acquisition card when the movable reflector is motionless; and when finding suspicious articles according to the terahertz image of a mail to be detected, the information processing module controls the movable reflector to move, and generates spectral information of the suspicious articles according to an electric signal sequence sent by the acquisition card during the movement of the movable reflector.

13 Claims, 3 Drawing Sheets

(52) U.S. Cl.
CPC ............ *G01N 2201/068* (2013.01); *G01N 2201/0633* (2013.01); *G01N 2201/12* (2013.01)

MAIL DETECTION DEVICE AND METHOD

CROSS-REFERENCE TO RELATED APPLICATIONS

This application is the 371 application of PCT Application No. PCT/CN2015/089536, filed Sep. 14, 2015, which is based upon and claims priority to Chinese Patent Application No. 201510470876.7, filed Aug. 4, 2015, the entire contents of which are incorporated herein by reference.

TECHNICAL FIELD

The present invention relates to the technical field of mail detection, in particular to a mail detection device and method.

BACKGROUND ART

Mails include postal mails and express mails. Generally, external packings and inclusions of mails are paper; non-paper articles may be included in mails; and even prohibited goods may be transferred by mail. Existing methods for detecting prohibited goods in mails mainly include: (1) using a metal detector to detect if the mails contain metal articles; (2) using X-rays to image mails and judging if the mails contain suspicious articles; (3) detecting if the mails contain poisons such as cocaine, marihuana and heroin through the sensitive smell of drug detector dogs.

However, the first mode applies to prohibited metal goods only; by the second mode, it can be only determined if there are suspicious articles, but participation of human or judgment by further detection measures is needed to judge whether the suspicious articles are prohibited goods, and X-rays are greatly harmful to human bodies; and the third mode applies to poisons only, and can be executed only after opening the mail. Therefore, those mail detection modes are limited in applicable scope, and the detection results are undesirable.

At present, terahertz technology has been still developing. Terahertz (THz in short) is a unit of frequency, which is equal to 1,000,000,000,000 Hz, and generally represents the frequency of electromagnetic waves. Terahertz waves refer to electromagnetic waves with frequencies in a range of 0.1 THz-10 THz, and like radio waves, terahertz waves can transmit the majority of non-polar materials, such as paper, wood and plastics. Besides, many materials show unique terahertz spectrum absorption characteristics, therefore categories of materials in mails can be identified through the terahertz spectrum absorption characteristics of materials.

SUMMARY OF THE INVENTION

In order to solve existing technical problems, the embodiments of the present invention provide a mail detection device and a mail detection method, which are able to accomplish prospective imaging of mails and acquire spectral information of suspicious articles of the mails.

The embodiments of the present invention employ the following technical solutions.

An embodiment of the present invention provides a mail detection device. The device includes a broad-band terahertz generator, a collimator, a beam splitter, a fixed reflector, a movable reflector, a wave buncher, a matrix detector, an acquisition card and an information processing module; wherein, the broad-band terahertz generator is used for generating and sending the broad-band initial terahertz waves;

the collimator is used for collimating the initial terahertz waves to form parallel terahertz waves;

the beam splitter is used for splitting the parallel terahertz waves into two beams, namely a first terahertz wave and a second terahertz wave;

the fixed reflector, the position fixed, is used for reflecting the first terahertz wave to form a first reflective terahertz wave;

the movable reflector, capable of moving to different positions, is used for reflecting the second terahertz wave to form a second reflective terahertz wave;

the wave buncher is used for bunching the first reflective terahertz wave and the second reflective terahertz wave to the matrix detector, wherein when the movable reflector moves and the first reflective terahertz wave and the second reflective terahertz wave form interference terahertz waves, the interference terahertz waves are bunched to the matrix detector;

the matrix detector is used for detecting intensity signals of the terahertz waves, converting the intensity signals of the terahertz waves into electric signals, and sending the electric signals to the acquisition card;

the acquisition card is used for acquiring the electric signals sent by the matrix detector and transmitting the electric signals to the information processing module;

the information processing module is used for generating a terahertz image of a mail to be detected according to the electric signals sent by the acquisition card when the movable reflector is motionless; and when finding suspicious articles according to the terahertz image of a mail to be detected, the information processing module controls the movable reflector to move, and generates spectral information of the suspicious articles according to the electric signal sequence sent by the acquisition card during the movement of the movable reflector.

In the above solution, the information processing module includes:

an image generating unit, for generating a terahertz image of a mail to be detected according to electric signals sent by the acquisition card when the movable reflector is motionless;

a movement control unit, for controlling the movable reflector to move when finding suspicious articles according to the terahertz image of the mail;

and a spectrum generating unit, for generating spectral information of suspicious articles according to the electric signal sequence sent by the acquisition card during the movement of the movable reflector.

In the above solution, the information processing module also includes:

a prohibited goods determination unit, for determining whether suspicious articles are prohibited goods according to the spectral information of the suspicious articles.

In the above solution, the information processing module also includes:

an alarm unit, for sending alarm information when it is determined that suspicious articles are prohibited goods according to the spectrum of the suspicious articles.

In the above solution, the device also includes:

a conveyor, positioned behind the collimator or in front of the wave buncher for conveying mails to be detected.

An embodiment of the present invention also provides a mail detection method. The method comprises the following steps:

generating and sending broad-band initial terahertz waves;

collimating the initial terahertz waves to form parallel terahertz waves;

splitting the parallel terahertz waves into two beams, namely a first terahertz wave and a second terahertz wave;

placing a fixed reflector in the transmission direction of the first terahertz wave to form the first reflective terahertz wave, and placing a movable reflector in the transmission direction of the second terahertz wave to form the second reflective terahertz wave;

bunching and the detecting the first and second reflective terahertz waves when the movable reflector is motionless, and the first reflective terahertz wave and the second reflective terahertz wave do not interfere with each other; converting the detected terahertz waves into electric signals, and generating a terahertz wave image of the mail to be detected according to the electric signals;

controlling the movable reflector to move so that the first reflective terahertz wave and the second reflective terahertz wave interfere with each other when finding suspicious articles according to the terahertz wave image of the mail to be detected, bunching and detecting the interfering terahertz waves during the movement of the movable reflector, converting the series of detected terahertz waves into an electric signal sequence, and generating the spectral information of the suspicious article according to the electric signal sequence;

placing the mail to be detected behind the parallel terahertz wave or in the front of the first reflective terahertz wave or the second reflective terahertz wave.

In the above solution, the step of finding the suspicious articles according to the terahertz image of the mail to be detected includes:

cutting the gray threshold segmentation on the terahertz image by using the OTSU method (OTSU algorithm) to transform into a binary image;

analyzing a connected domain of the binary image and determining pixel quantity; and confirming that the mail to be detected contains suspicious articles when the pixel quantity is greater than the pre-determined threshold.

In the above solution, the step of controlling the movable reflector to move includes:

controlling the movable reflector to move at a constant speed, wherein the movement speed is matched with the speed of detecting the terahertz wave.

In the above solution, the step of generating the spectral information of the suspicious articles includes:

acquiring information of the interference terahertz waves: $I(\delta)=\int_{-\infty}^{+\infty} B(v)\cos(2\pi v\delta)dv$; wherein $I(\delta)$ represents the signal strength of the interference terahertz waves when the optical path difference is $\delta$; v represents wave quantity; $B(v)$ represents the monochromatic light intensity after instrument characteristic correction when the wave quantity is v; and when v changes, $B(v)$ is spectrum;

performing Fourier transform on the information to obtain $B(v)=\int_{-\infty}^{+\infty} I(\delta)\cos(2\pi v\delta)d\delta$;

$I(\delta)$ is an even function, so $B(v)=2\int_{0}^{+\infty} I(\delta)\cos(2\pi v\delta)d\delta$, namely spectral information of the suspicious articles, is obtained.

In the above solution, the method also includes:

determining whether suspicious articles are prohibited goods according to the spectral information of the suspicious articles.

According to the mail detection device and the mail detection method provided by the embodiments of the present invention, broad-band terahertz waves are used as detection waves; through splitting a terahertz wave into beams and arranging to fix a fixed reflector and movable reflector, perspective imaging of the mail can be carried out, and the spectral information of the suspicious articles in the mail can also be obtained; meanwhile, the terahertz waves are used to replace the X-rays to image the mail, which can avoid injuring human bodies caused by X-rays; moreover, materials vary with terahertz spectrum absorption characteristics, so the solution is not limited in specific categories of prohibited goods.

DETAILED DESCRIPTION OF EMBODIMENTS

In order to clarify embodiments and technical solutions of the present invention, the technical solutions of the present invention are described in further detail below in junction with accompanying drawings and embodiments. Obviously, the described embodiments are only a part of embodiments of the present invention, not all the embodiments of the present invention. Based on the embodiments in the present invention, those skilled in the art can obtain other embodiments without creative labor, which all shall fall within the protective scope of the present invention.

Terms such as "first" and "second" are used for distinguishing the designated elements, not for sorting the designated elements or limiting the difference of the designated elements, and also not for limiting the scope of the present invention.

Figure 1:
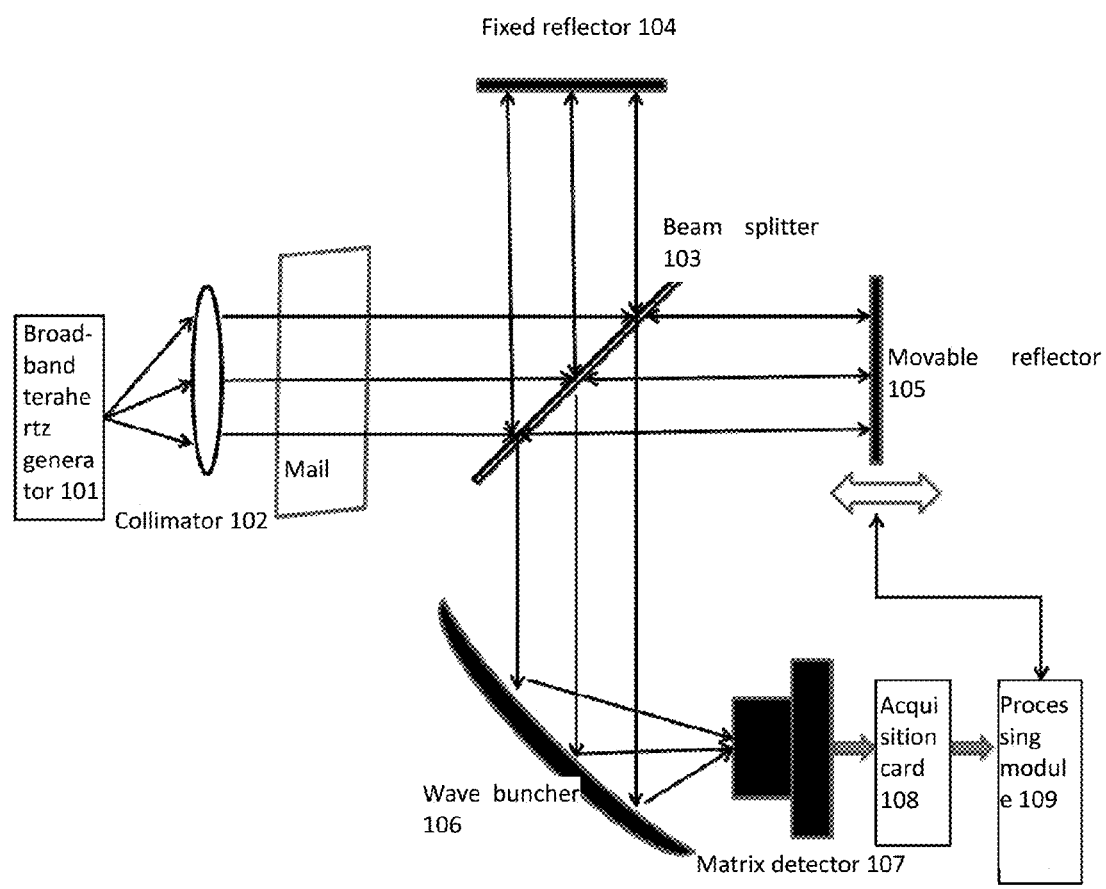
FIG. 1 is a structural view of a mail detection device according to an embodiment of the present invention.

FIG. 1 is a structural view of a mail detection device according to an embodiment of the present invention. As shown in FIG. 1, the device includes a broad-band terahertz generator 101, a collimator 102, a beam splitter 103, a fixed reflector 104, a movable reflector 105, a wave buncher 106, a matrix detector 107, an acquisition card 108 and an information processing module 109; wherein;

the broad-band terahertz generator 101 is used for generating and sending the broad-band initial terahertz waves;

the collimator 102 is used for collimating the initial terahertz waves to form parallel terahertz waves;

the beam splitter 103 is used for splitting the parallel terahertz waves into two beams, namely a first terahertz wave and a second terahertz wave;

the fixed reflector 104, the position fixed, is used for reflecting the first terahertz wave to form a first reflective terahertz wave;

the movable reflector 105, capable of moving to different positions, is used for reflecting the second terahertz wave to form a second reflective terahertz wave;

the wave buncher 106 is used for bunching the first reflective terahertz wave and the second reflective terahertz wave to the matrix detector 107, wherein when the movable reflector 105 moves and the first reflective terahertz wave and the second reflective terahertz wave form interference terahertz waves, the interference terahertz waves are bunched to the matrix detector 107;

the matrix detector 107 is used for detecting intensity signals of the terahertz waves, converting the intensity signals of the terahertz waves into electric signals, and sending the electric signals to the acquisition card 108;

the acquisition card 108 is used for acquiring the electric signals sent by the matrix detector 107 and transmitting the electric signals to the information processing module 109;

the information processing module 109 is used for generating a terahertz image of the mail to be detected according to the electric signals sent by the acquisition card 108 when the movable reflector 105 is motionless; and when finding suspicious articles according to the terahertz image of a mail to be detected, the information processing module controls the movable reflector 105 to move, and generates spectral information of the suspicious articles according to the electric signal sequence sent by the acquisition card 108 during the movement of the movable reflector 105.

Specifically, the terahertz wave generated and sent by the broad-band terahertz generator 101 is called initial terahertz waves, which includes terahertz waves of different frequencies (namely broad-band terahertz waves). Thus, it is ensured that when the terahertz waves irradiate on a mail to be detected, the terahertz waves of some frequencies, which can transmit suspicious articles, can be used for generating the spectral information of the suspicious articles even if the suspicious articles in the mail absorb the terahertz waves with some frequencies. In one embodiment, the frequencies of the initial terahertz waves are in a range of 0.2 THz-3 THz.

The collimator 102 may be a convex lens or an off-axis parabolic mirror. If the collimator is a convex lens, the convex lens is usually made from high-transparency resin (for example TPX) or high-density polyethylene (HDPE). Collimated by the collimator 102, the initial terahertz waves are called parallel terahertz waves.

In one embodiment, a mail to be detected is placed behind the collimator 102 so that the parallel terahertz waves irradiate on the mail to be detected. Some terahertz waves transmit the mail to be detected, and the terahertz waves which transmit the mail to be detected are still parallel terahertz waves.

The beam splitter 103 may be a half-transparent-half-reflecting mirror, which is used for splitting the parallel terahertz waves into two beams, namely a first terahertz wave and a second terahertz wave. The transmission directions of the first terahertz wave and the second terahertz wave are different.

The fixed reflector 104 may be a reflecting mirror, which is fixed at a point in the transmission direction of the first terahertz wave, and used for reflecting the first terahertz wave to form the first reflective terahertz wave.

The movable reflector 105 may be a reflecting mirror, which is fixed at a point in the transmission direction of the second terahertz wave, capable of moving along the transmission direction of the second terahertz wave, and used for reflecting the second terahertz wave to form the second reflective terahertz wave. The distance from a position where the movable reflector 105 stays in the motionless state to the beam spiller 103 is the same as the distance from the fixed reflector 104 to the beam splitter 103.

The first reflective terahertz wave and the second reflective terahertz wave irradiate on the beam splitter 103 again. The beam splitter is half-reflecting and half-transmitting for the terahertz wave, so the transmission direction of some of the first reflective terahertz wave and the second reflective terahertz wave, which pass through the beam splitter 103 is identical. The wave buncher 106 is disposed in the identical transmission direction of the terahertz waves to bunch the first reflective terahertz wave and the second reflective terahertz wave and send the waves to the matrix detector 107.

In one embodiment, a mail to be detected is placed in front of the wave buncher 106 so that the first reflective terahertz wave and the second reflective terahertz wave which pass through the beam splitter 103 irradiate on the mail to be detected. Some terahertz waves transmit the mail to be detected and irradiate on the wave buncher 106, which are bunched and sent to the matrix detector 107 by the wave buncher 106.

When the movable reflector 105 moves, the first reflective terahertz wave and the second reflective terahertz wave interfere with each other to form interference terahertz waves, and the wave buncher 106 bunches the interference terahertz waves and sends the waves to the matrix detector 107.

The matrix detector 107, which plays a role similar to a charge couple device (CCD) in a camera, is used for detecting intensity signals of the terahertz waves, converting the intensity signals of the terahertz waves into electric signals, and sending the electric signals to the acquisition card 108. Herein, the use of the matrix detector can greatly improve the speed of detecting the terahertz waves.

The acquisition card 108 acquires the electric signals sent by the matrix detector 107 and transmits the electric signals to the information processing module 109. The acquisition card 108 may be a data acquisition card, for example a data acquisition card PCI-9812 produced by ADLINK.

The information processing module 109 may be a central processing unit (CPU), a microcomputer (MPU), a digital signal processor (DSP) or a field programmable gate array (FPGA). When the movable reflector 105 is motionless, the information processing module 109 generates a terahertz image of a mail to be detected according to electric signals sent by the acquisition card 108; when finding suspicious articles in the terahertz image of the mail to be detected, the information processing module 109 controls the movable reflector 105 to move; then the first reflective terahertz wave and the second reflective terahertz wave will interfere with each other; and next, the matrix detector 107 detects and obtains signals of interference terahertz waves. During the movement of the movable reflector 105, the acquisition card 108 acquires a series of electric signals converted from terahertz waves which transmit the mail to be detected and suspicious articles therein, generates an electric signal sequence and sends the electric signal sequence to the information processing module 109. The information processing module 109 performs Fourier transform on the electric signal sequence to generate the spectral information of the suspicious articles.

Furthermore, in the mail detection device, the information processing module 109 may include:

an image generating unit, for generating a terahertz image of a mail to be detected according to electric signals sent by the acquisition card 108 when the movable reflector 105 is motionless;

a movement control unit, for controlling the movable reflector 105 to move when finding suspicious articles according to the terahertz image of the mail; and a spectrum generating unit, for generating spectral information of suspicious articles according to the electric signal sequence sent by the acquisition card 108 during the movement of the movable reflector 105.

Figure 2:
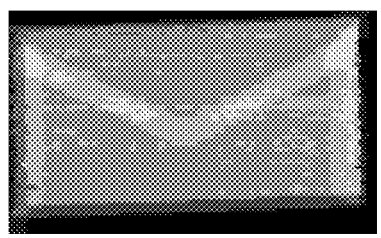
FIG. 2 is a schematic view of a terahertz image of a mail without suspicious articles according to an embodiment of the present invention.
Figure 3:
FIG. 3 is a schematic view of a terahertz image of a mail with suspicious articles according to an embodiment of the present invention.

Specifically, the distance from a position where the movable reflector 105 stays in the motionless state to the beam spiller 103 is the same as the distance from the fixed reflector 104 to the beam splitter 103, so the first reflective terahertz wave and the second reflective terahertz wave will not interfere with each other. In such circumstances, the image generating unit can generate a terahertz image of a mail to be detected according to electric signals sent by the acquisition card 108. The terahertz wave can transmit materials such as paper and plastics, so if the terahertz image of the mail to be detected is almost transparent, as shown in FIG. 2, it can be judged that the mail contains no suspicious articles, but when the terahertz image shows a dark or black area, it is judged that the mail contains suspicious articles. FIG. 3 illustrates an image of a key in the terahertz image of a mail when the mail contains a metal key.

In one embodiment, finding suspicious articles according to the terahertz image of a mail to be detected includes: carrying out gray threshold segmentation on the terahertz image by using the OTSU method (OTSU algorithm) to transform into a binary image, analyzing a connected domain of the binary image and judging pixel quantity; and when the pixel quantity is greater than a predetermined threshold, confirming that the mail to be detected contains suspicious articles. Herein, the predetermined threshold may be about 5%.

When finding suspicious articles according to terahertz image of the mail, the movement control unit controls the movable reflector 105 to move. In this way, the first reflective terahertz wave and the second reflective terahertz wave will interfere with each other because of an optical path difference.

Preferably, the movement control unit controls the movable reflector 105 to move at a constant speed, and the movement speed is matched with the speed of detecting the terahertz wave. This means that the movement speed of the movable reflector 105 is matched with the detection speed of the matrix detector 107. If the detection speed of the matrix detector 107 is lower, the movement speed of the movable reflector 105 should also be lower. On the contrary, if the detection speed of the matrix detector 107 is higher, the movement speed of the movable reflector 105 should also be higher. Generally, the movement speed of the movable reflector 105 is controlled to be in a range of 0.08 cm/s to 4.1 cm/s.

During the movement of the movable reflector 105, the matrix detector 107 detects a series of interference terahertz waves, and the acquisition card 108 also acquires a series of electric signals (namely electric signal sequence) and sends the electric signals to the information processing module 109. The spectrum generating unit can generate the spectral information of suspicious articles according to the electric signal sequence. Specifically, xy represents a two-dimensional image detected by the matrix detector, and λ represents a series of two-dimensional images obtained by the information processing module 109 each time when the movable reflector 105 moves. The series of images constitute a three-dimensional array. Every pixel point along the direction of λ is a one-dimensional array. Through Fourier transform carried out on the one-dimensional array, the spectral information of each pixel can be obtained.

More specifically, the spectrum generating unit generates the spectral information of suspicious articles by the following steps:

acquiring information of the interference terahertz waves: $I(\delta)=\int_{-\infty}^{+\infty}B(v)\cos(2\pi v\delta)dv$; wherein $I(\delta)$ represents the signal strength of the interference terahertz waves when the optical path difference is $\delta$; v represents wave quantity; $B(v)$ represents the monochromatic light intensity after instrument characteristic correction when the wave quantity is v; and when v changes, $B(v)$ is the spectrum;

performing Fourier transform on the information to obtain $B(v)=\int_{-\infty}^{+\infty}I(\delta)\cos(2\pi v\delta)d\delta$;

$I(\delta)$ is an even function, so $B(v)=2\int_{0}^{+\infty}I(\delta)\cos(2\pi v\delta)d\delta$, namely spectral information of the suspicious articles, is obtained.

Furthermore, in the mail detection device, the information processing module 109 also includes:

a prohibited goods determination unit, used for determining whether suspicious articles are prohibited goods according to the spectral information of the suspicious articles.

Specifically, categories of the suspicious articles can be determined according to the spectral information of the suspicious articles, thus whether suspicious articles are prohibited goods is determined. Determination of material categories through the spectrum is a prior art. Materials vary with characteristic absorption peaks which can be fingerprint spectrum of materials. Comparing the terahertz spectrum obtained through measurement with the spectral information in a spectrum database, when positions of the characteristic absorption peaks are overlapped, the specific categories of materials can be determined.

Furthermore, in the mail detection device, the information processing module 109 also includes:

an alarm unit, for sending alarm information when it is determined that suspicious articles are prohibited goods according to the spectrum of the suspicious articles.

Furthermore, any one of the above mail detection devices also includes:

a conveyor, positioned behind the collimator 102 or in front of the wave buncher 106 for conveying mails to be detected.

Figure 4:
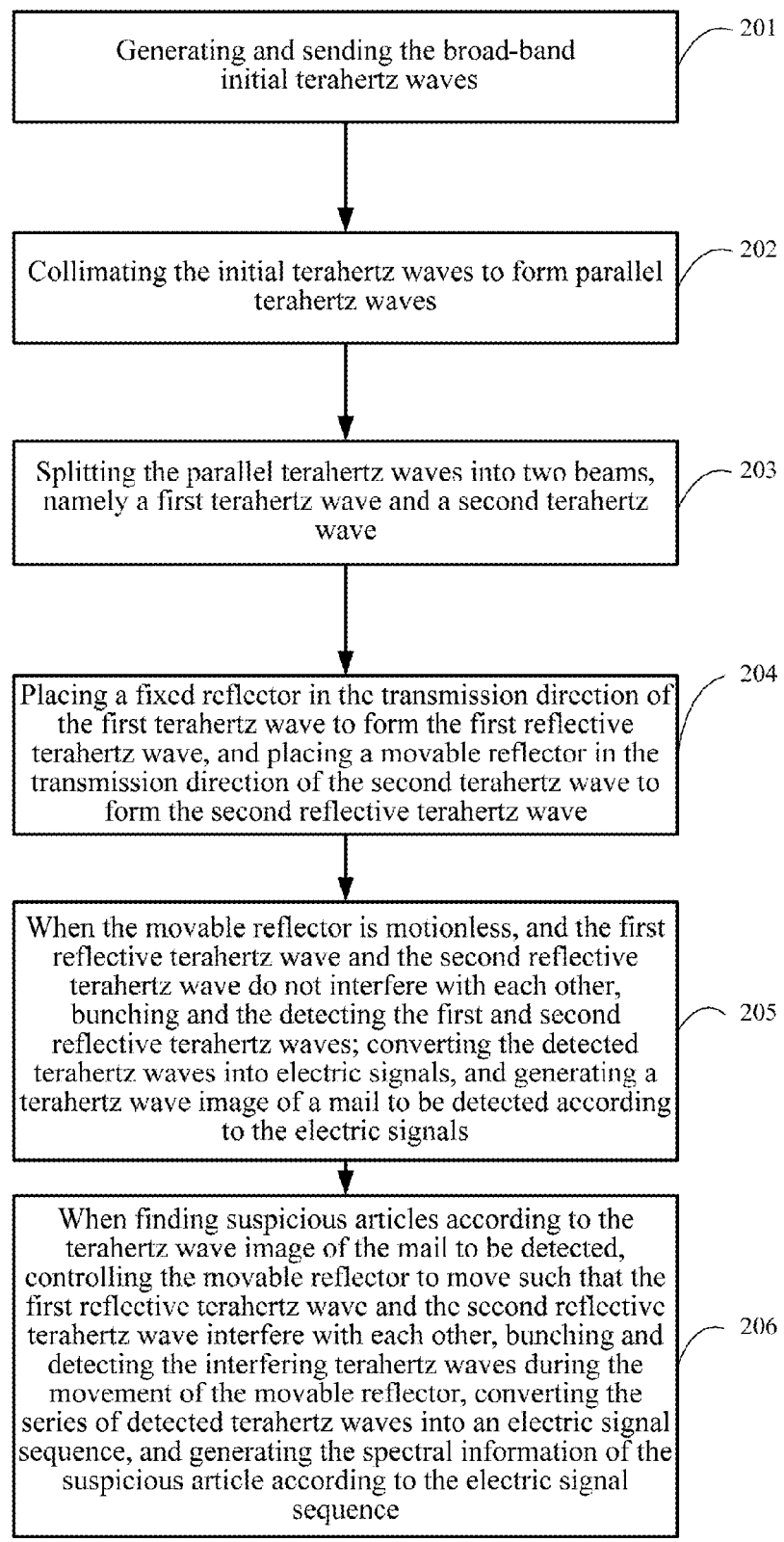
FIG. 4 is a flow chart of realization of the mail detection method according to an embodiment of the present invention.

An embodiment of the present invention also provides a mail detection method. As shown in FIG. 4, the method comprises the following steps:

step 201, generating and sending the broad-band initial terahertz waves;

step 202, collimating the initial terahertz waves to form parallel terahertz waves;

step 203, splitting the parallel terahertz waves into two beams, namely a first terahertz wave and a second terahertz wave;

step 204, placing a fixed reflector in the transmission direction of the first terahertz wave to form the first reflective terahertz wave, and placing a movable reflector in the transmission direction of the second terahertz wave to form the second reflective terahertz wave;

step 205, bunching and the detecting the first and second reflective terahertz waves when the movable reflector is motionless, and the first reflective terahertz wave and the second reflective terahertz wave do not interfere with each other; converting the detected terahertz waves into electric signals, and generating a terahertz wave image of a mail to be detected according to the electric signals;

step 206, controlling the movable reflector to move when finding suspicious articles according to the terahertz wave image of the mail to be detected, so that the reflective terahertz wave and the second reflective terahertz wave interfere with each other; bunching and detecting the interfering terahertz waves during the movement of the movable reflector, converting the series of detected terahertz waves into an electric signal sequence, and generating the spectral information of the suspicious article according to the electric signal sequence;

wherein, placing the mail to be detected behind the parallel terahertz wave or in the front of bunching the first reflective terahertz wave and the second reflective terahertz wave.

Furthermore, according to the above mail detection method, the step of finding the suspicious articles according to the terahertz image of the mail to be detected includes:

cutting the gray threshold segmentation on the terahertz image by using the OTSU method (OTSU algorithm) to transform into a binary image;

analyzing a connected domain of the binary image and judging pixel quantity; and confirming that the mail to be detected contains suspicious articles when the pixel quantity is greater than a predetermined threshold.

Furthermore, according to the above mail detection method, the step of controlling the movable reflector to move includes:

controlling the movable reflector to move at a constant speed, wherein the movement speed is matched with the speed of detecting the terahertz wave.

Furthermore, according to the above mail detection method, the step of generating the spectral information of the suspicious articles includes:

acquiring information of the interference terahertz waves: $I(\delta)=\int_{-\infty}^{+\infty} B(v)\cos(2\pi v\delta)dv$; wherein $I(\delta)$ represents the signal strength of the interference terahertz waves when the optical path difference is $\delta$; v represents wave quantity; $B(v)$ represents the monochromatic light intensity after instrument characteristic correction when the wave quantity is v; and when v changes, $B(v)$ is the spectrum;

performing Fourier inversion on the information to obtain $B(v)=\int_{-\infty}^{+\infty} I(\delta)\cos(2\pi v\delta)d\delta$;

$I(\delta)$ is an even function, so $B(v)=2\int_{0}^{+\infty} I(\delta)\cos(2\pi v\delta)d\delta$, namely spectral information of the suspicious articles, is obtained.

The mail detection method may also include:

determining whether suspicious articles are prohibited goods according to the spectral information of the suspicious articles.

Those skilled in the art should understand that the embodiments of the present invention can be provided as methods, systems or computer program products. Therefore, the embodiments of the present invention can be hardware embodiments, software embodiments or embodiments in combination of software and hardware. Besides, the present invention can be one or more computer program products implemented in computer readable media (including but not limited to magnetic disc memory, optical memory, etc.) which contain program codes for computers.

The present invention is described with reference to the flow charts and/or block diagrams of the methods, devices (systems) and computer program products of the embodiments of the present invention. It should be understood that the computer program commands realize every process and/or block in the flow charts and/or block diagrams, and the combination of processes and/or blocks in the flow charts and/or block diagrams. The computer program command can be supplied to the processor of a universal computer, a special computer, an embedded processing machine or other programmable data processing devices to generate a machine, so the commands executed by the processor of the computer or other programmable data processing devices generate a device for realizing specific functions in one or more processes in the flow charts and/or one or more blocks in the block diagrams.

The computer program commands can also be stored in computer readable memories which guide the computer or other data processing devices to work in a specific mode, so the commands stored in the computer readable memories generate products including command devices, and the command devices conduct specific functions in one or more steps in the flow charts and/or one or more blocks in the block diagrams.

The computer program commands can also be loaded in the computer or other programmable data processing devices so that computer or other programmable data processing devices execute a series of operations to generate processing executed by the computer. Thus, the commands executed in the computer or other programmable data processing devices supply steps of conducting specific functions in one or more processes in the flow charts and/or one or more blocks in the block diagrams.

The above embodiments are merely preferable embodiments of the present invention and do not limit the protective scope of the present invention.

What is claimed is:

1. A mail detection device, characterized in that the device comprises a broad-band terahertz generator, a collimator, a beam splitter, a fixed reflector, a movable reflector, a wave buncher, a matrix detector, an acquisition card and an information processing module; wherein, the broad-band terahertz generator is used for generating and sending initial terahertz waves of the broad band;

the collimator is used for collimating the initial terahertz waves to form parallel terahertz waves;

the beam splitter is used for splitting the parallel terahertz waves into two beams, namely a first terahertz wave and a second terahertz wave;

the fixed reflector, position fixed, is used for reflecting the first terahertz wave to form a first reflective terahertz wave;

the movable reflector, capable of moving to different positions, is used for reflecting the second terahertz wave to form a second reflective terahertz wave;

the wave buncher is used for bunching the first reflective terahertz wave and the second reflective terahertz wave to the matrix detector, wherein when the movable reflector moves and the first reflective terahertz wave and the second reflective terahertz wave form interference terahertz waves, the interference terahertz waves are bunched to the matrix detector;

the matrix detector is used for detecting intensity signals of the terahertz waves, converting the intensity signals of the terahertz waves into electric signals, and sending the electric signals to the acquisition card;

the acquisition card is used for acquiring the electric signals sent by the matrix detector and transmitting the electric signals to the information processing module;

the information processing module is used for generating a terahertz image of a mail to be detected according to the electric signals sent by the acquisition card when the movable reflector is motionless; and when finding suspicious articles according to the terahertz image of a mail to be detected, the information processing module controls the movable reflector to move, and generates spectral information of the suspicious articles according to an electric signal sequence sent by the acquisition card during the movement of the movable reflector.

2. The mail detection device according to claim 1, characterized in that the information processing module comprises:
    an image generating unit, for generating a terahertz image of a mail to be detected according to electric signals sent by the acquisition card when the movable reflector is motionless;
    a movement control unit, for controlling the movable reflector to move when finding suspicious articles according to the terahertz image of the mail; and
    a spectrum generating unit, for generating spectral information of suspicious articles according to the electric signal sequence sent by the acquisition card during the movement of the movable reflector.

3. The mail detection device according to claim 2, characterized in that the information processing module also comprises:
    a prohibited goods determination unit, which is used for determining whether suspicious articles are prohibited goods according to the spectral information of the suspicious articles.

4. The mail detection device according to claim 3, characterized in that the information processing module also comprises:
    an alarm unit, for sending alarm information when it is determined that suspicious articles are prohibited goods according to the spectrum of the suspicious articles.

5. The mail detection device according to claim 4, characterized in that the device also comprises:
    a conveyor, positioned behind the collimator or in front of the wave buncher for conveying mail to be detected.

6. The mail detection device according to of claim 3, characterized in that the device also comprises:
    a conveyor, positioned behind the collimator or in front of the wave buncher for conveying mail to be detected.

7. The mail detection device according to claim 2, characterized in that the device al so comprises:
    a conveyor, positioned behind the collimator or in front of the wave buncher for conveying mail to be detected.

8. The mail detection device according to claim 1, characterized in that the device also comprises:
    a conveyor, positioned behind the collimator or in front of the wave buncher for conveying mail to be detected.

9. A mail detection method, characterized in that the method comprises:
    generating and sending the broad-band initial terahertz waves;
    collimating the initial terahertz waves to form parallel terahertz waves;
    splitting the parallel terahertz waves into two beams, namely a first terahertz wave and a second terahertz wave;
    placing a fixed reflector in the transmission direction of the first terahertz wave to form the first reflective terahertz wave, and placing a movable reflector in the transmission direction of the second terahertz wave to form the second reflective terahertz wave;
    bunching and the detecting the first and second reflective terahertz waves when the movable reflector is motionless, and the first reflective terahertz wave and the second reflective terahertz wave do not interfere with each other; converting the detected terahertz waves into electric signals, and generating a terahertz wave image of a mail to be detected according to the electric signals;
    controlling the movable reflector to move when finding suspicious articles according to the terahertz wave image of the mail to be detected, so that the first reflective terahertz wave and the second reflective terahertz wave interfere with each other; bunching and detecting the interfering terahertz waves during the movement of the movable reflector, converting the series of detected terahertz waves into an electric signal sequence, and generating the spectral information of the suspicious article according to the electric signal sequence;
    placing the mail to be detected behind the parallel terahertz wave or in the front of the first reflective terahertz wave and the second reflective terahertz wave.

10. The mail detection method according to claim 9, characterized in that the step of finding the suspicious articles according to the terahertz image of the mail to be detected comprises:
    cutting the gray threshold segmentation on the terahertz image by using the OTSU method (OTSU algorithm) to transform into a binary image;
    analyzing a connected domain of the binary image and judging pixel quantity; and
    confirming that the mail to be detected contains suspicious articles when the pixel quantity is greater than a predetermined threshold.

11. The mail detection method according to claim 9, characterized in that the step of controlling the movable reflector to move comprises:
    controlling the movable reflector to move at a constant speed, wherein the movement speed is matched with the speed of detecting the terahertz wave.

12. The mail detection method according to claim 9, characterized in that the step of generating the spectral information of suspicious articles comprises:
    acquiring information of the interference terahertz waves: $I(\delta)=\int_{-\infty}^{+\infty}B(v)\cos(2\pi v\delta)dv$; wherein $I(\delta)$ represents the signal strength of the interference terahertz waves when the optical path difference is $\delta$; v represents wave quantity; $B(v)$ represents the monochromatic light intensity after instrument characteristic correction when the wave quantity is v; and when v changes, $B(v)$ is the spectrum;
    performing Fourier inversion on the information to obtain $B(v)=\int_{-\infty}^{+\infty}I(\delta)\cos(2\pi v\delta)d\delta$;
    $I(\delta)$ is an even function, so $B(v)=2\pi\int_{-\infty}^{+\infty}I(\delta)\text{con}(2\pi v\delta)d\delta$, namely spectral information of the suspicious articles, is obtained.

13. The mail detection method according to claim 9, characterized in that the method also comprises:
    determining whether suspicious articles are prohibited goods according to the spectral information of the suspicious articles.

* * * * *